United States Patent
Ito et al.

(10) Patent No.: US 11,219,496 B2
(45) Date of Patent: Jan. 11, 2022

(54) SURGICAL TOOL, MEDICAL TREATMENT INSTRUMENT, AND SURGICAL SYSTEM

(71) Applicant: MEDICAROID CORPORATION, Kobe (JP)

(72) Inventors: Tetsushi Ito, Kobe (JP); Kazutoshi Kan, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 168 days.

(21) Appl. No.: 16/262,949

(22) Filed: Jan. 31, 2019

(65) Prior Publication Data

US 2019/0201149 A1 Jul. 4, 2019

Related U.S. Application Data

(63) Continuation of application No. PCT/JP2018/011612, filed on Mar. 23, 2018.

(51) Int. Cl.
| | |
|---|---|
| A61B 34/00 | (2016.01) |
| A61B 34/30 | (2016.01) |
| A61B 34/37 | (2016.01) |
| A61B 34/35 | (2016.01) |
| A61B 17/29 | (2006.01) |

(Continued)

(52) U.S. Cl.
CPC .............. *A61B 34/71* (2016.02); *A61B 17/29* (2013.01); *A61B 34/30* (2016.02); *A61B 34/35* (2016.02); *A61B 34/37* (2016.02); *A61B 2017/003* (2013.01); *A61B 2017/00314* (2013.01); *A61B 2017/00323* (2013.01); *A61B 2017/2905* (2013.01); *A61B 2017/2906* (2013.01); *A61B 2017/3445* (2013.01); *A61B 2017/3447* (2013.01); *A61B 2034/302* (2016.02); *A61B 2034/305* (2016.02); *A61B 2034/715* (2016.02)

(58) Field of Classification Search
CPC .............. A61B 34/71; A61B 2034/305; A61B 2034/715
See application file for complete search history.

(56) References Cited

U.S. PATENT DOCUMENTS

| | | |
|---|---|---|
| 9,259,274 B2 | 2/2016 | Prisco |
| 9,775,677 B2 | 10/2017 | Hyodo et al. |
| 2010/0015570 A1 | 1/2010 | Kutzner et al. |

(Continued)

FOREIGN PATENT DOCUMENTS

| | | |
|---|---|---|
| JP | 2006-061364 A | 3/2006 |
| JP | 2010-022837 A | 2/2010 |

(Continued)

*Primary Examiner* — Melanie R Tyson
*Assistant Examiner* — Mohammed S Adam
(74) *Attorney, Agent, or Firm* — Metrolex IP Law Group, PLLC

(57) ABSTRACT

A surgical tool according to one or more embodiment may include: an end effector; an elongate element that drives the end effector; a hollow shaft that includes a proximal end portion and a distal end portion which is coupled to the end effector; a driving member which the elongate element led via the shaft is wound on; a guide pulley that is disposed between the proximal end portion of the shaft and the driving member and guides the elongate element; and a tension pulley that is disposed between the proximal end portion of the shaft and the guide pulley and biases the elongate element.

14 Claims, 7 Drawing Sheets

(51) Int. Cl.
    *A61B 17/00*    (2006.01)
    *A61B 17/34*    (2006.01)

(56) References Cited

U.S. PATENT DOCUMENTS

| | | |
|---|---|---|
| 2010/0022837 A1* | 1/2010 | Ishiguro et al. |
| 2014/0257333 A1* | 9/2014 | Blumenkranz .... A61B 17/2909 606/130 |
| 2016/0135663 A1 | 5/2016 | Isoda et al. |
| 2017/0105805 A1 | 4/2017 | Hasegawa et al. |
| 2018/0080533 A1 | 3/2018 | Awtar |
| 2018/0215051 A1 | 8/2018 | Kan |

FOREIGN PATENT DOCUMENTS

| | | |
|---|---|---|
| JP | 2010-253162 A | 11/2010 |
| JP | 2012-504016 A | 2/2012 |
| JP | 2013-103074 A | 5/2013 |
| JP | 2015-024007 A | 2/2015 |
| JP | 2016-000432 A | 1/2016 |
| JP | 2016-016242 A | 2/2016 |
| WO | 2008/136160 A1 | 11/2008 |
| WO | 2016/161449 A1 | 10/2016 |
| WO | 2017/006374 A1 | 1/2017 |

* cited by examiner

SURGICAL TOOL, MEDICAL TREATMENT INSTRUMENT, AND SURGICAL SYSTEM

CROSS-REFERENCE TO RELATED APPLICATION

This application is a continuation of international application No. PCT/JP2018/011612 filed on Mar. 23, 2018, which claims priority to Japanese Patent Application No. 2017-059891 filed on Mar. 24, 2017, the entire contents of which is incorporated herein by reference.

BACKGROUND

The disclosure relates to tension adjusting mechanisms for elongate elements that drive end effectors used for surgical tools and other purposes, and interfaces and driving mechanisms including the tension adjusting mechanisms.

In recent years, robotic surgical systems have been used in fields such as endoscopic surgery. In a medical treatment instrument used for a robotic surgical system, for example, elongate elements such as wires are engaged with end effectors with jaws and the like. When a driving mechanism including gears is driven, the elongate elements are pulled in or fed out, driving the end effectors.

Such elongate elements may get loose or slack, for example, for the reason that tension is exerted on them for a long time. To address this problem, medical treatment instruments have been developed in which the tensions of elongate elements can be adjusted using springs or the like.

For example, Patent Document 1 (Published Japanese Translation of PCT International Patent Application No. 2012-504016) and Patent Document 2 (Japanese Patent Application Publication No. 2013-103074) disclose medical treatment instruments in which the tensions of the elongate elements are adjusted by springs or the like via which parts of the elongate elements are attached to the housing.

In addition, Patent Document 3 (Japanese Patent Application Publication No. 2016-016242) discloses a medical treatment instrument in which the tensions of elongate elements are adjusted in such a way that two pulleys, on which the elongate elements are wound, are coupled to each other via springs or the like.

SUMMARY

Meanwhile, in the case of a driving mechanism including tension adjusting mechanisms for adjusting the tensions of elongate elements, there has been a problem that parts such as springs are required, increasing the parts count in the driving mechanism, which in turn increases the size of the driving mechanism. In addition, increasing the degree of freedom of an end effector makes the structure of the driving mechanism complicated, making it more difficult to mount the tension adjusting mechanisms and downsize the driving mechanism.

An object of an embodiment of the disclosure is to provide a tension adjusting mechanism that is small but capable of adjusting the tension of an elongate element for driving an end effector, and an interface and driving mechanism including the tension adjusting mechanisms.

A surgical tool according to an aspect of one or more embodiments may include: an end effector; a elongate element that drives the end effector; a hollow shaft that includes a proximal end portion and a distal end portion which is coupled to the end effector; a driving member which the elongate element led via the shaft is wound on; a guide pulley that is disposed between the proximal end portion of the shaft and the driving member and guides the elongate element; and a tension pulley that is disposed between the proximal end portion of the shaft and the guide pulley and biases the elongate element.

A medical treatment instrument according to an aspect of one or more embodiments may include: surgical tools each including an end effector and a flexible shaft; driving devices to which the surgical tools are attached respectively; and an outer tube that holds the shafts of the surgical tools. Each of the surgical tools includes: the end effector; a elongate element that drives the end effector; the shaft that is hollow and includes a proximal end portion and a distal end portion which is coupled to the end effector; a driving member which the elongate element led via the shaft is wound on; a guide pulley that is disposed between the proximal end portion of the shaft and the driving member and guides the elongate element; and a tension pulley that is disposed between the proximal end portion of the shaft and the guide pulley and biases the elongate element.

A surgical system according to an aspect of one or more embodiments may include: surgical tools each including an end effector and a flexible shaft; driving devices to which the surgical tools are attached respectively; an outer tube that holds the shafts of the surgical tools; and a supporting device including holding portions that hold the respective driving devices and a grasping portion that grasps the outer tube. Each of the surgical tools includes: the end effector; a elongate element that drives the end effector; the shaft that is hollow and includes a proximal end portion and a distal end portion which is coupled to the end effector; a driving member which the elongate element led via the shaft is wound on; a guide pulley that is disposed between the proximal end portion of the shaft and the driving member and guides the elongate element; and a tension pulley that is disposed between the proximal end portion of the shaft and the guide pulley and biases the elongate element.

DETAILED DESCRIPTION

Figure 1:
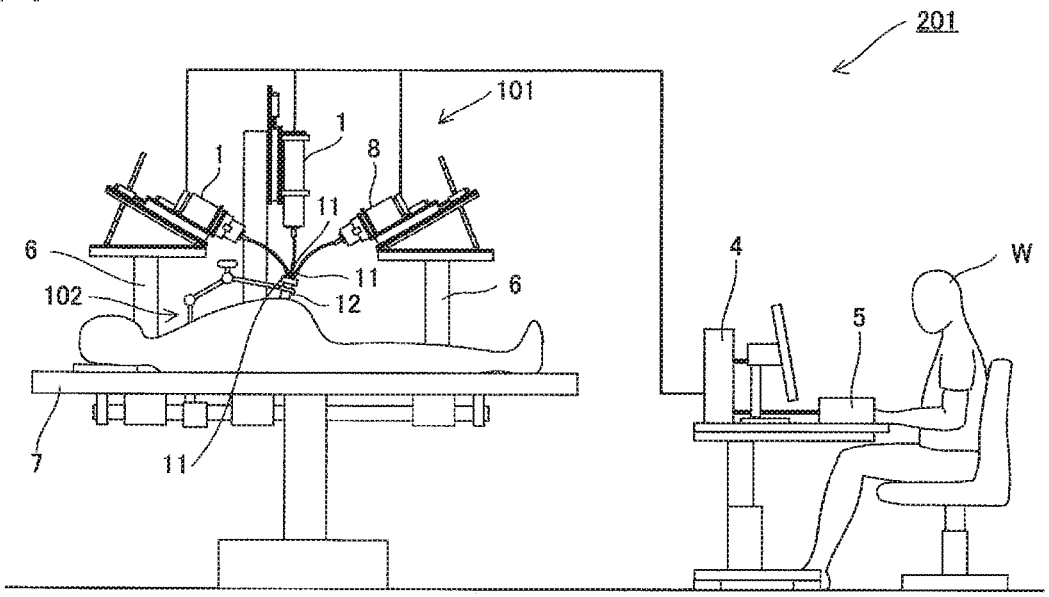
FIG. 1 is a diagram illustrating a view of the structure of a surgical system according to one or more embodiments.

Descriptions are provided hereinbelow for embodiments based on the drawings. In the respective drawings referenced herein, the same constituents are designated by the same reference numerals and duplicate explanation concerning the same constituents is omitted. All of the drawings are provided to illustrate the respective examples only.

<Surgical System>

FIG. 1 is a diagram illustrating the structure of a surgical system according to one or more embodiments.

Referring to FIG. 1, the surgical system 201 includes a medical treatment instrument 101, controller 4, and operation unit 5. A surgeon W operates the medical treatment instrument 101 remotely to perform, for example, an endoscopic surgery.

The medical treatment instrument 101 includes, for example, one or more surgical tools 1, one or more endoscopes 8, one or more guide tubes 11 into which distal ends of the surgical tools 1 and the endoscopes 8 are inserted, and a bundling tube 12 into which the one or more guide tubes 11 are inserted. The surgical tools 1 and the endoscopes 8 are supported by, for example, support tables 6 attached to a treatment table 7.

The surgical tools 1, endoscopes 8, guide tubes 11, and operation unit 5 are electrically connected to the controller 4. When the operation unit 5 is operated by the surgeon W, the operation unit 5 gives operation instructions to the surgical tools 1, the endoscopes 8 and the guide tubes 11 via the controller 4. This allows the surgeon W to remotely operate the surgical tools 1, the endoscopes 8, and the guide tubes 11.

<Medical Treatment Instrument>

Figure 2:
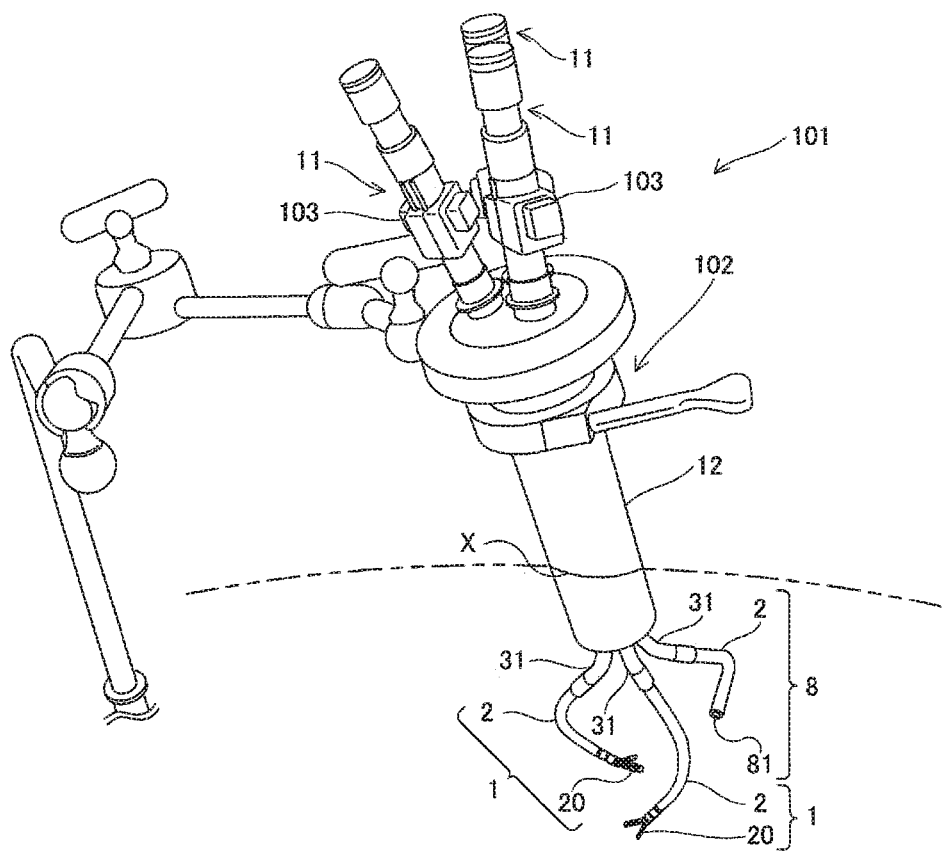
FIG. 2 is a diagram illustrating a perspective view of the structure of a medical treatment instrument according to one or more embodiments.

FIG. 2 is a perspective view of the structure of the medical treatment instrument according to one or more embodiments. FIG. 2 illustrates the medical treatment instrument 101 part of which is inside the body of the patient but is seen through the body. The body surface of the patient is indicated by the dashed double-dotted lines, and an incised portion X formed in the body surface of the patient is indicated by the continuous line.

Referring to FIG. 2, the surgical tool 1 has a flexible shaft 2 in an elongated shape and a distal end portion 20 deposed at the distal end of the flexible shaft 2. In FIG. 2, the distal end portion 20 and part of the flexible shaft 2 pass through the guide tube 11 and are exposed from the guide tube 11.

The endoscope 8 has a flexible shaft 2 in an elongated shape and a camera 81 disposed at the distal end of the flexible shaft 2. In FIG. 2, the camera 81 and part of the flexible shaft 2 pass through the guide tube 11 and is exposed from the guide tube 11.

The guide tube 11 is made of, for example, soft plastic, such as polypropylene and vinyl chloride. The guide tube 11 has a not-illustrated wire member and a guide-tube-bending adjustment mechanism 103 that operates the wire member.

The guide-tube-bending adjustment mechanism 103 is, for example, a mechanism that adjusts manually the pulling length of the wire member, also fixes the wire member by screwing so that the wire member does not move, and electrically adjusts the pulling length of the wire member by using a not-illustrated motor and gears with which the wire member is engaged. The guide-tube-bending adjustment mechanism 103, in this way, adjusts the pulling length of the wire member to bend a bending portion 31 of the guide tube 11.

The bundling tube 12 is made of, for example, soft plastic, such as polypropylene or vinyl chloride. The bundling tube 12 is flexible and has a tubular shape the inner diameter of which is larger than the outer diameter of the guide tube 11.

For example, when a laparoscopic surgery is performed, the bundling tube 12 is inserted through an incised portion X formed in the body surface of the patient into the body cavity. Note that the bundling tube 12 may be inserted through a natural hole, such as the oral cavity, into the body of the patient, instead of through the incised portion X. In other words, the medical treatment instrument 101 may be used not only for laparoscopic surgeries but also for natural orifice transluminal endoscopic surgeries.

The bundling tube 12 is grasped at the outer wall, for example, at the proximal end thereof, in other words, on the side which is not inserted into the body surface, by a grasping mechanism 102, so that the position and orientation of the bundling tube 12 is fixed.

For the laparoscopic surgery, since the bundling tube 12 is inserted into the body cavity, for example, through an incised portion X formed in the body surface of the patient, it is more difficult to fix the position and orientation of the bundling tube 12 than in the case where the bundling tube 12 is inserted through a natural hole, such as the oral cavity. For this reason, the grasping mechanism 102 for grasping the bundling tube 12 as above is especially useful in the case of grasping a medical treatment instrument used for a laparoscopic surgery.

Figure 3:
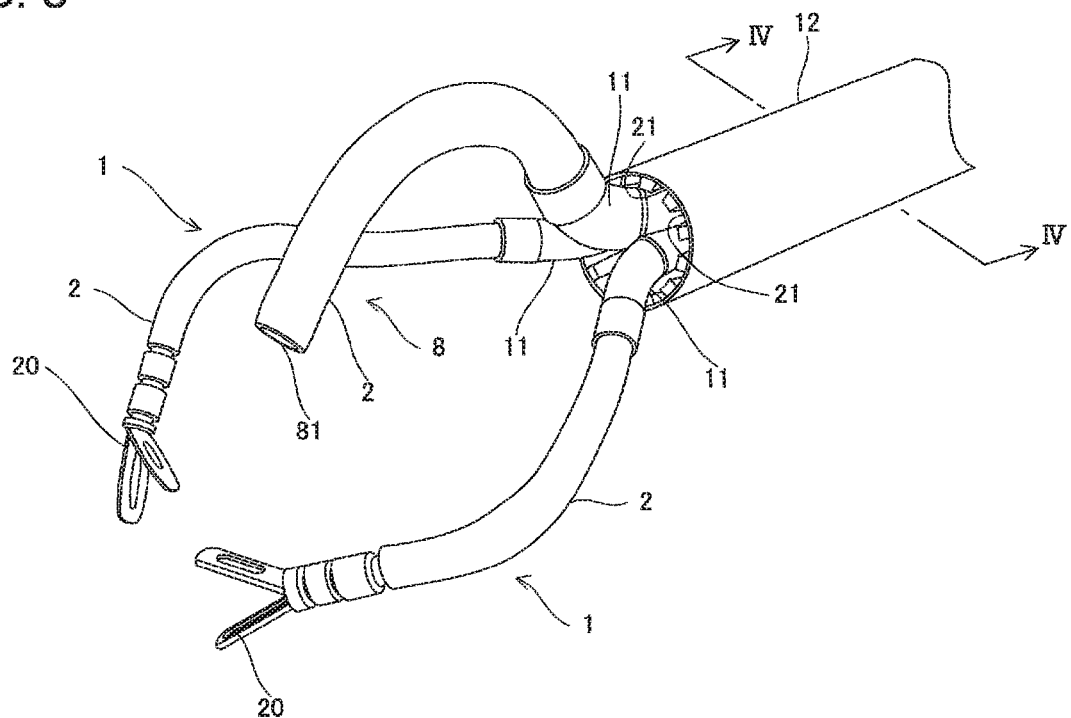
FIG. 3 is a diagram illustrating a perspective view of guide tubes inserted in a bundling tube.
Figure 4:
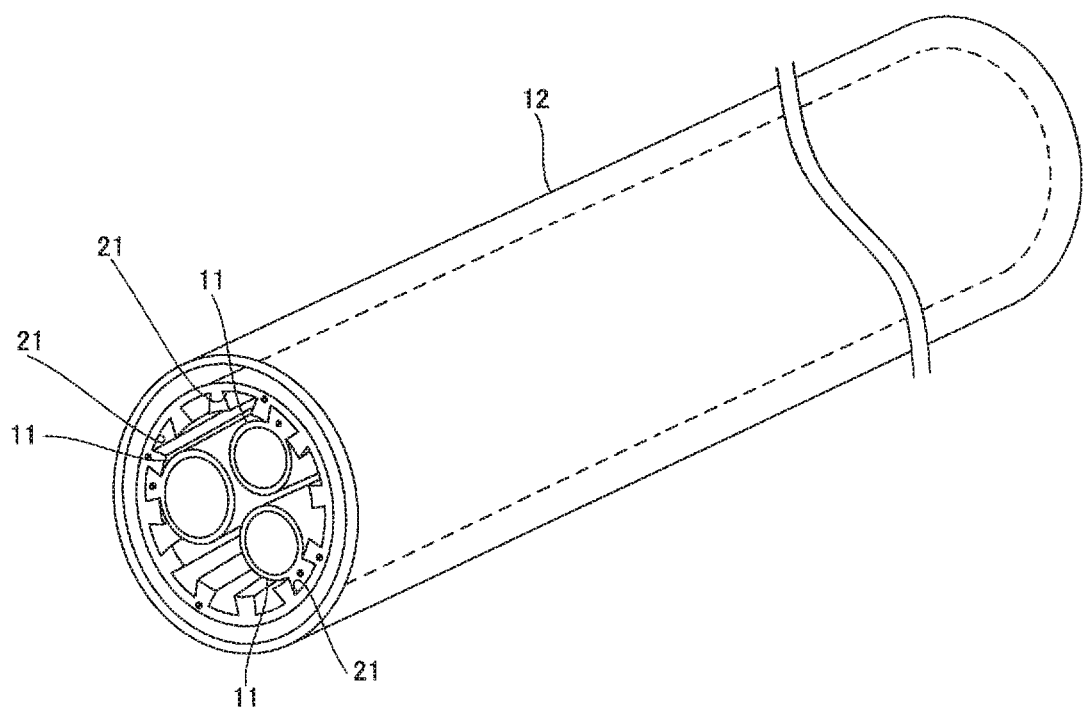
FIG. 4 is a diagram illustrating a cross-sectional perspective view taken along line IV-IV in FIG. 3.

FIG. 3 is a perspective view of the guide tubes passing through the inside of the bundling tube. FIG. 4 is a cross-sectional perspective view taken along line IV-IV in FIG. 3.

Referring to FIGS. 3 and 4, the bundling tube 12 has one or more guides 21 that guide insertion of the guide tubes 11. The guides 21, for example, are dovetail grooves formed on the inner wall of the bundling tube 12 and extending in the axial direction of the bundling tube 12. As illustrated in FIG. 4, each guide 21 has an approximately trapezoidal cross-sectional shape the width of which increases gradually from the inner circumferential surface toward the outer circumferential surface of the bundling tube 12.

Note that as described above, the bundling tube 12 is flexible and can be bent at an appropriate angle to be inserted into the body cavity.

Figure 5:
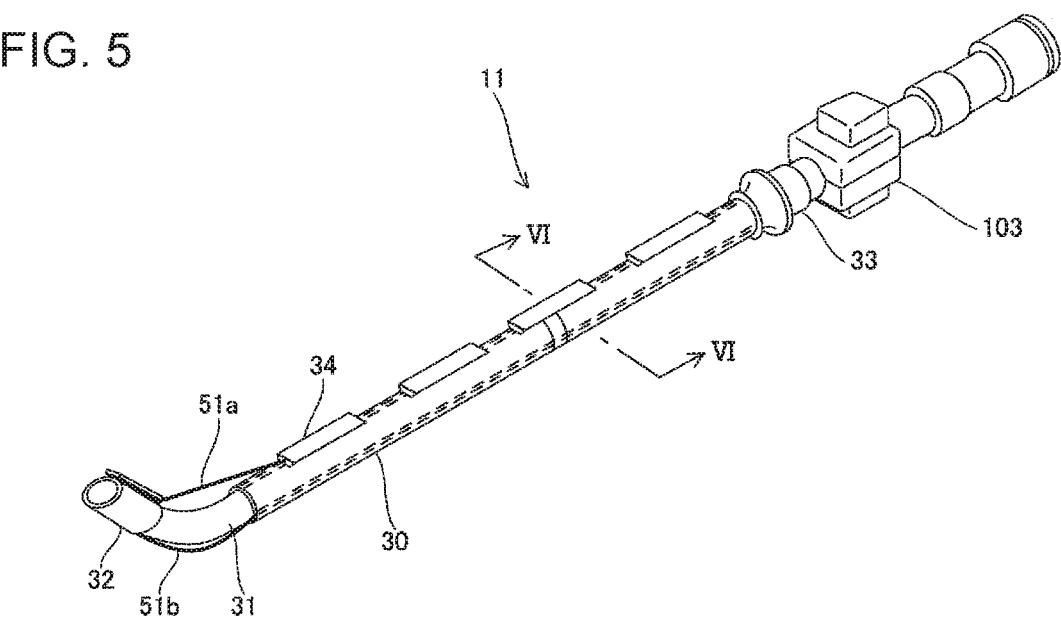
FIG. 5 is a diagram illustrating a perspective view of the structure of a guide tube according to one or more embodiments.

FIG. 5 is a perspective view of the structure of a guide tube according to one or more embodiments.

Referring to FIG. 5, the guide tube 11 includes a flexible sleeve 30, bending portion 31, guide-tube distal end portion 32, and guide-tube proximal end portion 33. The guide tube 11 also has engaging portions 34 formed intermittently on the outer peripheral surface of the sleeve 30 and extending in the axial direction of the guide tube 11.

In the state where the guide tube 11 is inserted into the bundling tube 12 as illustrated in FIGS. 3 and 4, at least part of the bending portion 31 and the guide-tube distal end portion 32 are exposed from the bundling tube 12.

Figure 6:
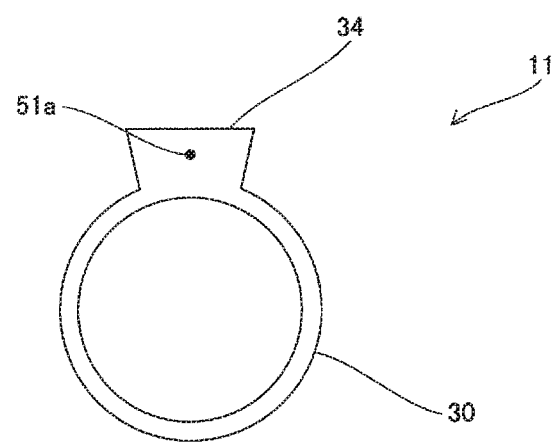
FIG. 6 is a diagram illustrating a cross-sectional view taken along line VI-VI in FIG. 5.

FIG. 6 is a cross-sectional view taken along line VI-VI in FIG. 5.

Referring to FIG. 6, the engaging portion 34 is projected from the outer peripheral surface of the guide tube 11 and, for example, has an approximately trapezoidal cross-sectional shape the width of which gradually increases as the engaging portion 34 extends outwardly in the radial direction of the guide tube 11.

When the guide tube 11 is inserted into the bundling tube 12 illustrated in FIGS. 3 and 4, the engaging portions 34 are slidably engaged with the guide 21 of the bundling tube 12. This structure, in the state where the guide tube 11 is inserted into the bundling tube 12, makes it possible to keep the positional relationship between the guide tube 11 and the bundling tube 12 even when the position or orientation of the medical treatment instrument 101 is changed.

In addition, since the engaging portions 34 are formed intermittently in the axial direction of the guide tube 11 as described above, the guide tube 11 can be easily inserted or removed from the bundling tube 12 even when the bundling tube 12 is bent. Note that the engaging portion 34 can be formed continuously in the axial direction of the sleeve 30.

The guide tube 11 has wire members 51*a* and 51*b* as illustrated in FIG. 5 as operating elements for operating the guide tube 11. The wire member 51*a* passes through the insides of the engaging portions 34, and the first end side of the wire member 51*a* is fixed to the guide-tube distal end portion 32. The wire member 51*b* passes through the inside of the sleeve 30, and the first end side of the wire member 51*b* is fixed to the guide-tube distal end portion 32. Then, the guide-tube-bending adjustment mechanism 103 pulls in or feeds out the second end side of the wire member 51*a* or the second end side of the wire member 51*b* to bend the bending portion 31.

Note that in the case where the accurate positional relationship between the bundling tube 12 and the guide tube 11 does not need to be kept when the position and angle of the medical treatment instrument 101 is adjusted, the bundling tube 12 does not need to have the guides 21 as described above, and the guide tube 11 does not need to have the engaging portions 34 as described above.

In addition, referring to FIG. 5 again, although the guide tube 11 has the wire members 51*a* and 51*b* as the operating elements for operating the guide tube 11, the guide tube 11 may have, for example, rods, flat plates, or the combination of rods and flat plates that are connected to be bendable, instead of the wire members 51*a* and 51*b*.

In addition, as the operating elements, the wire member 51*a* may be combined with rods and flat plates. For example, of the above operating element, the part passing through the engaging portions 34 may be a wire member 51*a* and the exposed part connecting the engaging portion 34 and the guide-tube distal end portion 32 may be rods connected to be bendable.

<Surgical Tool>

[Outline Structure]

Figure 7:
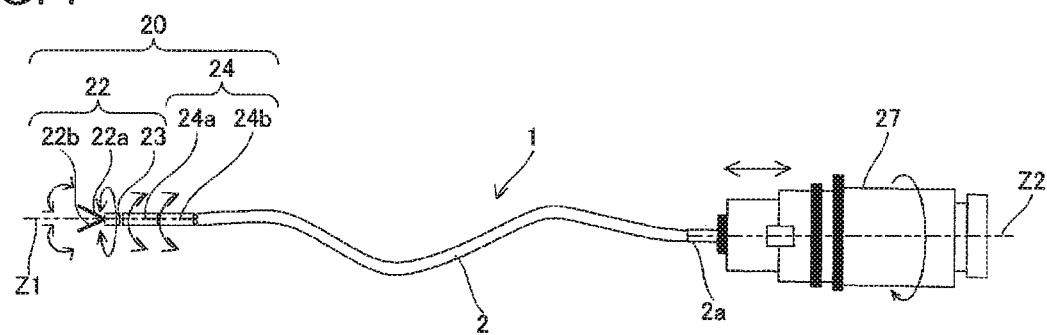
FIG. 7 is a diagram illustrating a diagram illustrating an outline structure of a surgical tool according to one or more embodiments.

FIG. 7 is a diagram illustrating an outline structure of the surgical tool according to one or more embodiments.

As illustrated in FIG. 7, the surgical tool 1 has the distal end portion 20, the flexible shaft 2, and a surgical-tool driving mechanism 27. The distal end portion 20 has an end effector 22, such as grasping forceps, and a multi-articulated portion 24. The end effector 22 has a first jaw 22*a*, second jaw 22*b*, and wrist portion 23. The multi-articulated portion 24 has a first multi-articulated portion 24*a* and a second multi-articulated portion 24*b*.

Note that the end effector 22 is not limited to the grasping forceps but may be a scalpel or a hook.

To each of the first jaw 22*a*, second jaw 22*b*, wrist portion 23, first multi-articulated portion 24*a*, and second multi-articulated portion 24*b* is fixed an elongate element, such as a wire or a cable, described later.

The flexible shaft 2 has a proximal end portion 2*a* at the opposite end from the distal end portion 20 side end. The proximal end portion 2*a* is coupled to the surgical-tool driving mechanism 27 so that the flexible shaft 2 itself is rotatable.

The wrist portion 23 has a shape extending in a specific direction. Specifically, the wrist portion 23 has the first jaw 22*a* and second jaw 22*b* coupled to the first end in the longitudinal direction of the wrist portion 23 itself and the multi-articulated portion 24 coupled at its second end. The wrist portion 23 is rotatable on the distal end axis Z1 extending in the longitudinal direction of the wrist portion 23 itself.

Figure 8:
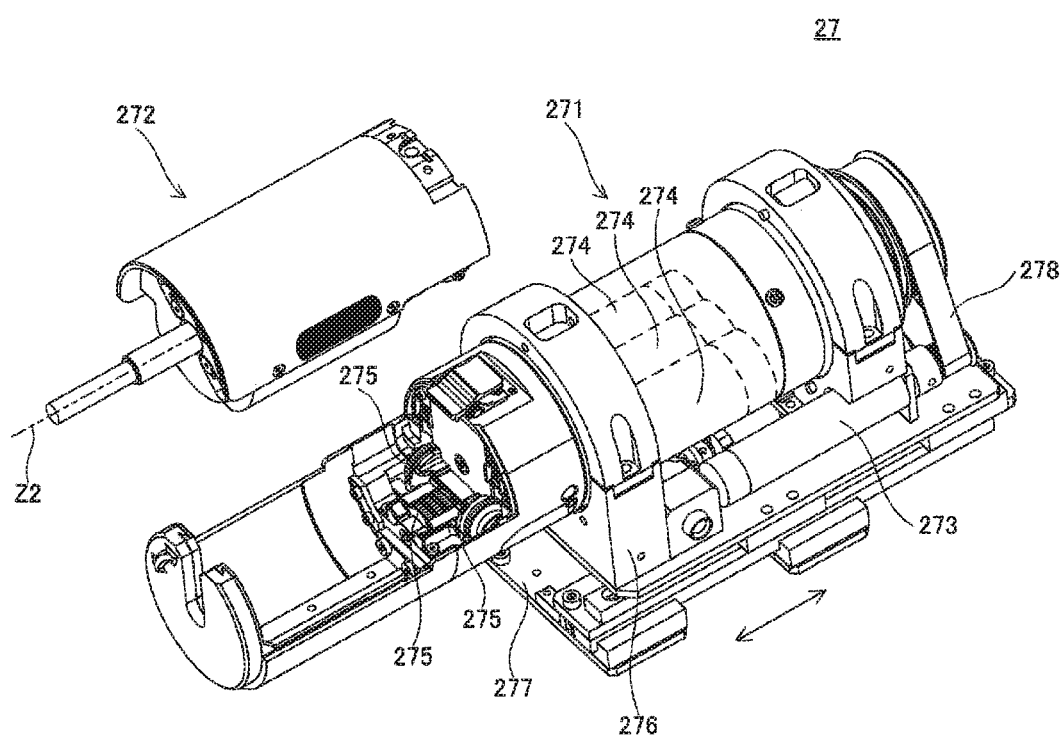
FIG. 8 is a diagram illustrating a view of the structure of a surgical-tool driving mechanism, such as is illustrated in FIG. 7, with an interface separated.
Figure 9:
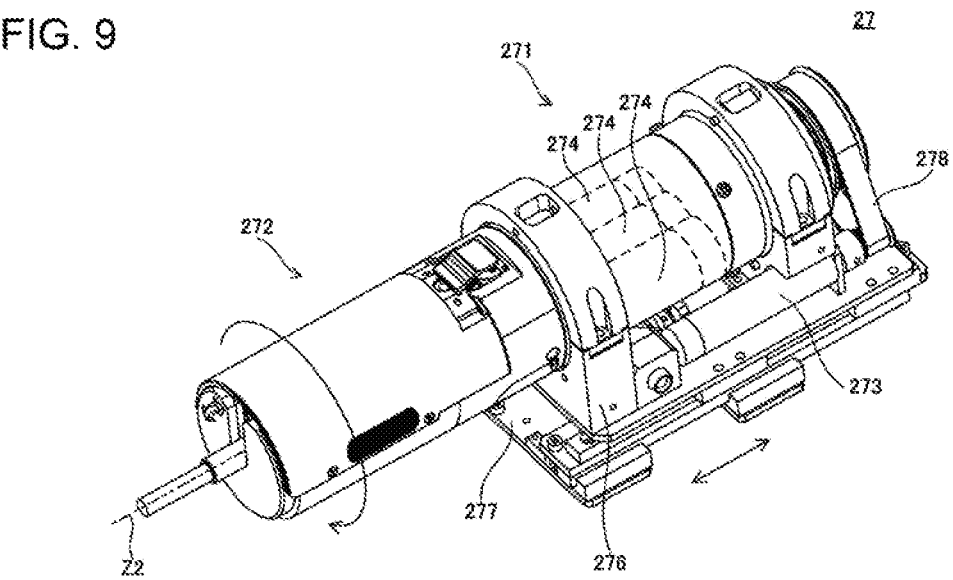
FIG. 9 is a diagram illustrating a view of the structure of a surgical-tool driving mechanism, such as is illustrated in FIG. 7, with the interface attached.

FIG. 8 is a diagram illustrating the structure of a surgical-tool driving mechanism, such as is illustrated in FIG. 7, with the interface separated. FIG. 9 is a diagram illustrating the structure of a surgical-tool driving mechanism, such as is illustrated in FIG. 7, with the interface attached.

Referring to FIGS. 8 and 9, the surgical-tool driving mechanism 27 has a driving device 271 at the distal end portion 20, the interface 272 attached to the driving device 271, a supporting device 276 supporting the driving device 271, and a base 277 slidably supporting the supporting device 276. FIG. 8 illustrates the interface separated state, in other words, the state where the interface 272 is removed from the driving device 271, and FIG. 9 illustrates the interface attached state, in other words, the state where the interface 272 is attached to the driving device 271.

The driving device 271 has first driving sources 274 and transmission members 275 that transmit forces generated by driving of the first driving sources 274. The interface 272 includes inside, transmission-counterpart members and driving pulleys (serving as driving members) described later.

In the surgical-tool driving mechanism 27 according to one or more embodiments, the first driving sources 274 are motors, and the transmission members 275 and the transmission-counterpart members are gears. In the state where the interface 272 is attached to the driving device 271, the transmission members 275 are engaged with the transmission-counterpart members. In this state, when a first driving source 274 is driven, a transmission member 275 and the transmission-counterpart member engaged with the transmission member 275 rotate.

Note that the transmission members 275 and the transmission-counterpart members may be, for example, racks and pinions. In other words, one of the transmission member 275 and the transmission-counterpart member may be a circular gear, and the other may be a flat plate with grooves engaged with the circular gear. Alternatively, both of the transmission member 275 and the transmission-counterpart member may be members different from gears.

To the driving pulleys included inside the interface 272 are wound wires respectively fixed to the first jaw 22*a*, second jaw 22*b*, wrist portion 23, first multi-articulated portion 24*a*, and second multi-articulated portion 24*b* illustrated in FIG. 7. When the wires wound to the respective driving pulleys are operated, the first jaw 22*a*, second jaw 22b, wrist portion 23, first multi-articulated portion 24a, and second multi-articulated portion 24b operate separately.

On the supporting device 276 is mounted a second driving source 273. When the second driving source 273 is driven, the rotational force of the second driving source 273 is transmitted to the driving device 271 via a belt 278, rotating the driving device 271 and the interface 272 illustrated in FIG. 9 on the proximal end axis Z2 extending in the longitudinal direction of the proximal end portion 2a illustrated in FIG. 7. In addition, on the base 277 is mounted a not-illustrated third driving source. When the third driving source is driven, the supporting device 276 supporting the driving device 271 moves along the proximal end axis Z2.

Thus, the surgical tool 1 according to one or more embodiments is configured to be operable, for example, with 7 degrees of freedom as indicated by the arrows in FIG. 7. Note that the surgical tool 1 may be configured to be operable with 3 to 6 degrees of freedom, for example, by combining the movements of the first jaw 22a and the second jaw 22b instead of having two separate movements, eliminating one of the first multi-articulated portion 24a and the second multi-articulated portion 24b, or limiting at least one of the slide movement of the supporting device 276 and the rotational movement of the driving device 271 on the driving mechanism 27.

[Structure of Distal End Portion]
(Multi-Articulated Portion)

Figure 10A:
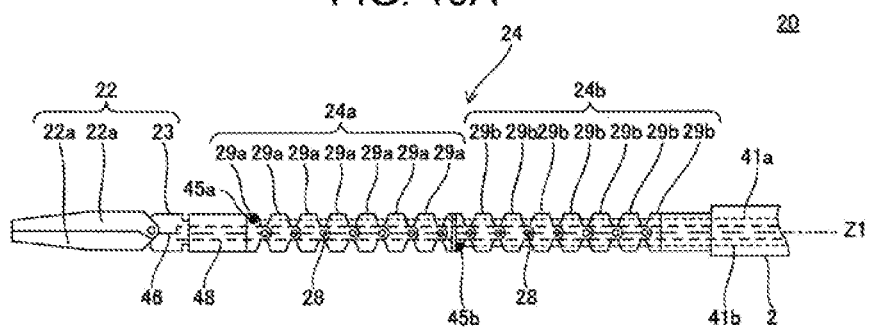
FIG. 10A is a diagram illustrating a view of the structure of a distal end portion of a surgical tool, such as is illustrated in FIG. 7.
Figure 10B:
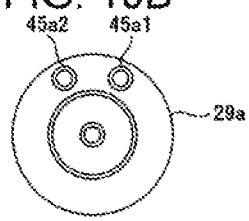
FIG. 10B is a diagram illustrating a view of the structure of a distal end portion of a surgical tool, such as is illustrated in FIG. 7.
Figure 10C:
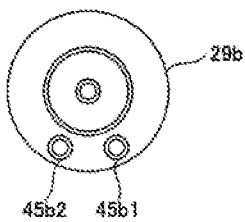
FIG. 10C is a diagram illustrating a view of the structure of a distal end portion of a surgical tool, such as is illustrated in FIG. 7.

FIGS. 10A to 10C are diagrams illustrating the structure of a distal end portion of a surgical tool, such as is illustrated in FIG. 7. FIG. 10A illustrates the detailed structure of the multi-articulated portion at the distal end portion, FIG. 10B illustrates the state where a multi-articulated portion operating wire, such as is illustrated in FIG. 10A is fixed at the first articulated portion, and FIG. 10C illustrates the state where a multi-articulated portion operating wire, such as is illustrated in FIG. 10A is fixed at the second first multi-articulated portion.

As illustrated in FIG. 10A, the first multi-articulated portion 24a and the second multi-articulated portion 24b at the distal end portion 20 have piece members 29a and piece members 29b, respectively, aligned continuously in a line via pins 28 along the distal end axis Z1.

Each of the piece members 29a and 29b has a columnar shape extending in the extending direction of the distal end axis Z1. Both ends of the columnar part of each of the piece members 29a and 29b are tapered.

A multi-articulated portion operating wire 41a extending along the distal end axis Z1 passes through the piece members 29a and the piece members 29b. In addition, a multi-articulated portion operating wire 41b extending along the distal end axis Z1 passes through the piece members 29b.

As illustrated in FIG. 10B, both ends of the multi-articulated portion operating wire 41a are fixed to distal end side fixing points 45a1 and 45a2 of the first articulated portion 24a. In addition, as illustrated in FIG. 10C, both ends of the multi-articulated portion operating wire 41b are fixed to distal end side fixing points 45b1 and 45b2 of the second multi-articulated portion 24b.

When the surgical-tool driving mechanism 27 illustrated in FIG. 7 pulls in one end of the multi-articulated portion operating wire 41a, the first multi-articulated portion 24a bends. When the surgical-tool driving mechanism 27 illustrated in FIG. 7 pulls in one end of the multi-articulated portion operating wire 41b, the first multi-articulated portion 24b bends. The structure described above in which the first multi-articulated portion 24a and the second multi-articulated portion 24b can bend independently of each other enables the multi-articulated portion 24 to be bent into complicated shapes such as an S-shaped curve.

(Wrist Portion)

Figure 11:
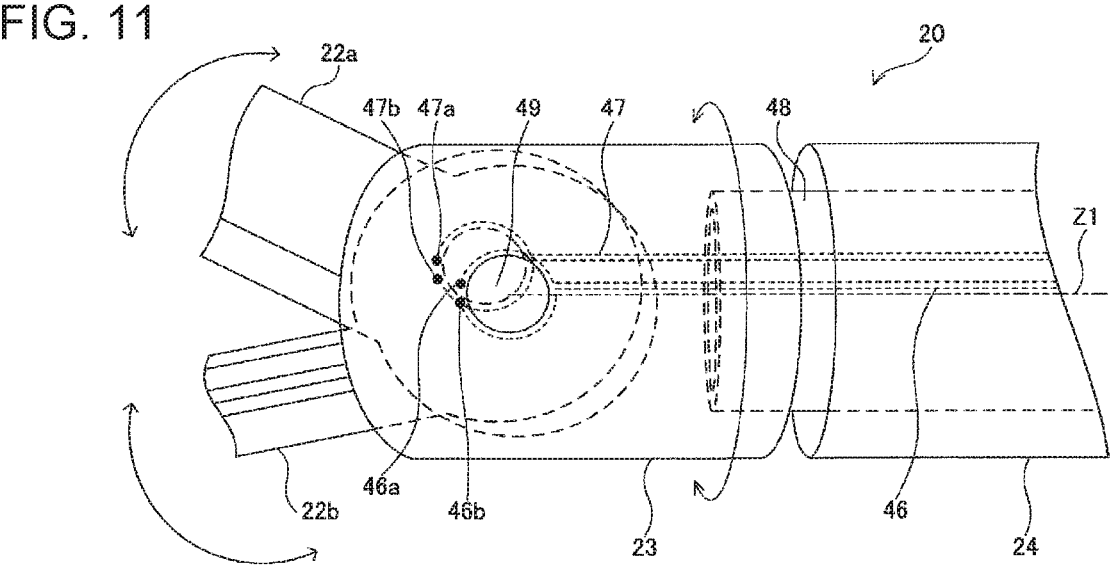
FIG. 11 is a diagram illustrating a view of the structure of a wrist portion, such as is illustrated in FIG. 10A.

FIG. 11 is a diagram illustrating the structure of a wrist portion, such as is illustrated in FIG. 10A.

Referring to FIG. 11, a torque transmission tube 48 passes through the inside of the multi-articulated portion 24. More specifically, the torque transmission tube 48 passes through the insides of the multi-articulated portion 24 and the flexible shaft 2 illustrated in FIG. 7, and the first end of the torque transmission tube 48 is fixed to the wrist portion 23, and the second end thereof is rotatably coupled to the surgical-tool driving mechanism 27.

When the surgical-tool driving mechanism 27 rotates the torque transmission tube 48 on the proximal end axis Z2, the wrist portion 23 fixed to the torque transmission tube 48 and the first jaw 22a and second jaw 22b coupled to the wrist portion 23 rotate on the distal end axis Z1.

Note that the wrist portion 23 may be rotated using a wire instead of the torque transmission tube 48. In this case, the mechanism for rotating the wrist portion 23 has, for example, a structure disclosed in Patent Document 4 (International Patent Application Publication WO2017/006374).

In other words, the wrist portion 23 has, in its inside, a not-illustrated groove formed in the circumferential direction of a circle the center of which the distal end axis Z1 passes at. Instead of the torque transmission tube 48, a first wire and a second wire are used. The first wire passes through part of the above groove, and the second wire passes through part of the above groove that the first wire does not pass through.

When the surgical-tool driving mechanism 27 pulls in the first wire or the second wire, the wrist portion 23 and the first jaw 22a and second jaw 22b coupled to the wrist portion 23 rotate on the distal end axis Z1.

(Jaws)

As illustrated in FIG. 11, two jaw operating wires 46 and 47 pass through the inside of the wrist portion 23. The jaw operating wire 46 couples the surgical-tool driving mechanism 27 illustrated in FIG. 7 and the first jaw 22a to each other. The jaw operating wire 47 couples the surgical-tool driving mechanism 27 illustrated in FIG. 7 and the second jaw 22b to each other.

More specifically, the first end 46a and the second end 46b of the jaw operating wire 46 are fixed to the first jaw 22a. When the surgical-tool driving mechanism 27 pulls in the first end 46a or the second end 46b, the first jaw 22a pivots about a coupling axis 49 disposed in the wrist portion 23.

The first end 47a and the second end 47b of the jaw operating wire 47 are fixed to the second jaw 22b. When the surgical-tool driving mechanism 27 pulls in or feeds out the first end 47a or the second end 47b along the proximal end axis Z2, the second jaw 22b pivots about the coupling axis 49.

[Surgical-Tool Driving Mechanism]

Figure 12:
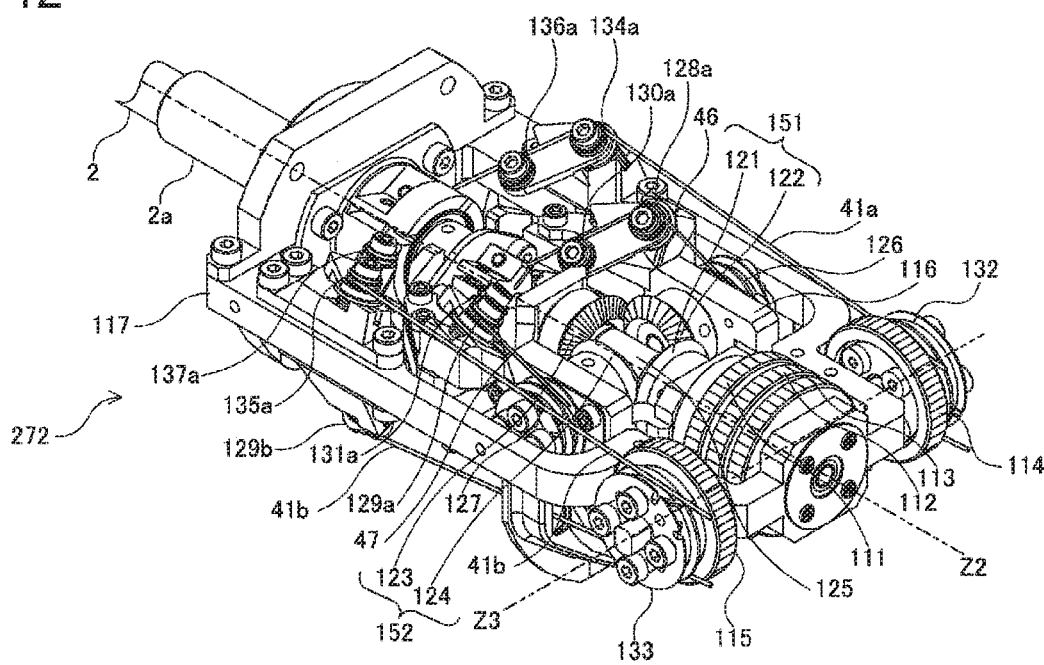
FIG. 12 is a diagram illustrating a perspective view of the structure of the interface in the surgical-tool driving mechanism according to one or more embodiments.
Figure 13:
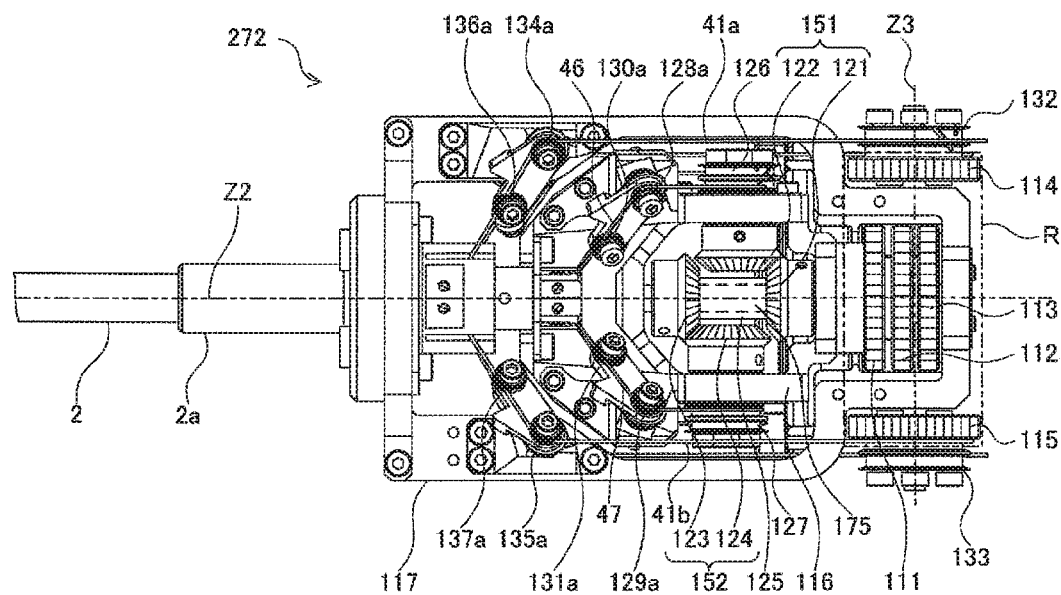
FIG. 13 is a diagram illustrating a plan view of a structure of an interface, such as is illustrated in FIG. 12.
Figure 14:
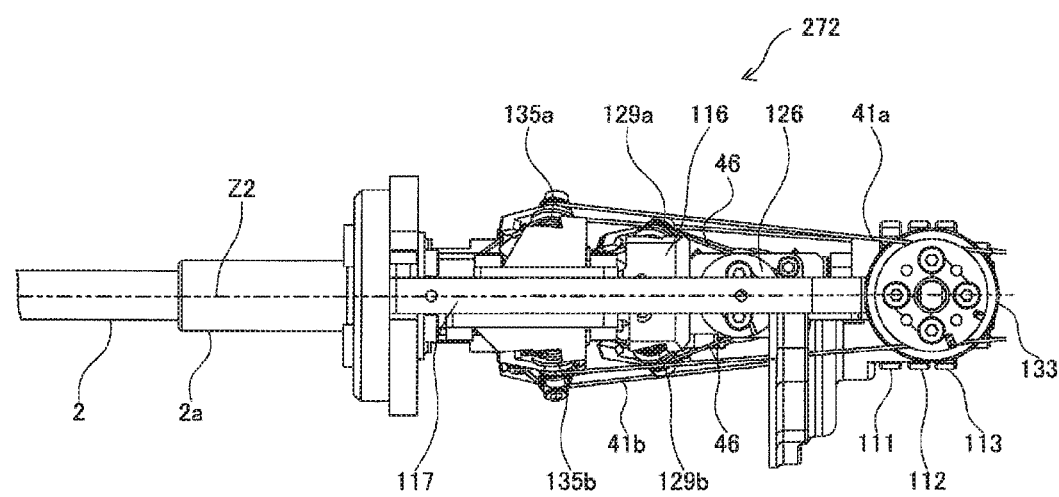
FIG. 14 is a diagram illustrating a side view of the structure of an interface, such as is illustrated in FIG. 12.

FIG. 12 is a perspective view of the structure of the interface in the surgical-tool driving mechanism according to one or more embodiments. FIG. 13 is a plan view of the structure of an interface, such as is illustrated in FIG. 12. FIG. 14 is a side view of the structure of an interface, such as is illustrated in FIG. 12. FIGS. 12 to 14 illustrates the inside structure of the interface 272.

Referring to FIGS. 12 to 14, the interface 272 in the surgical-tool driving mechanism 27 has a wrist-portion driving gear 111, first jaw driving gear 112, second jaw driving gear 113, first-multi-articulated-portion driving gear 114, second-multi-articulated-portion driving gear 115, base 116, and frame 117.

The wrist-portion driving gear 111, first jaw driving gear 112, second jaw driving gear 113, first-multi-articulated-portion driving gear 114, and second-multi-articulated-portion driving gear 115 are the transmission-counterpart members and engaged with the respective transmission members 275 illustrated in FIG. 8. The wrist-portion driving gear 111, first jaw driving gear 112, second jaw driving gear 113, first-multi-articulated-portion driving gear 114, and second-multi-articulated-portion driving gear 115 drive the wrist portion 23, first jaw 22a, second jaw 22b, first multi-articulated portion 24a, and second multi-articulated portion 24b, respectively.

The wrist-portion driving gear 111, first jaw driving gear 112, second jaw driving gear 113, and base 116 are disposed inside the frame 117. On the other hand, the first-multi-articulated-portion driving gear 114 and the second-multi-articulated-portion driving gear 115 are disposed outside the frame 117.

When the wrist-portion driving gear 111, first jaw driving gear 112, and second jaw driving gear 113 are defined as "the first gears", and the first-multi-articulated-portion driving gear 114 and second-multi-articulated-portion driving gear 115 are defined as "the second gears", the rotation axis of the first gears and the rotation axis of the second gears intersect with each other. More specifically, the rotation axis of the first gears extends along the proximal end axis Z2, and the rotation axis of the second gears extends in a direction orthogonal to the proximal end axis Z2.

This structure allows more arrangement variations, for example, than in the case where the gears are disposed such that their rotation axes are in parallel.

More specifically, the wrist-portion driving gear 111, first jaw driving gear 112, and second jaw driving gear 113 have approximately the same shape. For example, all of the wrist-portion driving gear 111, first jaw driving gear 112, and second jaw driving gear 113 rotate on the proximal end axis Z2.

The first-multi-articulated-portion driving gear 114 and the second-multi-articulated-portion driving gear 115 have approximately the same shape. For example, the first-multi-articulated-portion driving gear 114 and the second-multi-articulated-portion driving gear 115 rotate on an orthogonal axis Z3 which is orthogonal to the proximal end axis Z2.

In addition, as illustrated in FIG. 13, in a plan view along the direction of the normal line of the plane including the proximal end axis Z2 and the orthogonal axis Z3, in other words, in a plan view along the direction of looking down at the frame 117, the three gears that rotate on the proximal end axis Z2—in other words, the wrist-portion driving gear 111, first jaw driving gear 112, and second jaw driving gear 113—are disposed within the length of the first-multi-articulated-portion driving gear 114 and the second-multi-articulated-portion driving gear 115 in the direction along the proximal end axis Z2. This structure allows the interface 272 to have the gears arranged within an area R, good for space saving, illustrated in FIG. 13.

As described above, the above described one or more embodiments makes the arrangement area for the transmission-counterpart members small, contributing space-saving.
(Driving Mechanism for Wrist Portion)

The base 116 has a frame shape enclosing four bevel gears 121, 122, 123, and 124 described later. The base 116 is fixed to the wrist-portion driving gear 111 and transmits the torque of the wrist-portion driving gear 111 to the wrist portion 23 illustrated in FIG. 7.

Specifically, when the wrist-portion driving gear 111 rotates according to an operation instruction from the controller 4 illustrated in FIG. 1, the base 116 fixed to the wrist-portion driving gear 111 rotates on the proximal end axis Z2. The torque transmission tube 48 passes through the inside of the flexible shaft 2, coupling the base 116 and the wrist portion 23. The torque transmission tube 48 rotates inside the flexible shaft 2 along with the rotation of the base 116, rotating on the distal end axis Z1, the wrist portion 23 illustrated in FIG. 11, to which the torque transmission tube 48 is fixed.

Along with the rotation of the wrist portion 23, the first jaw 22a and second jaw 22b illustrated in FIG. 7, coupled to the wrist portion 23 rotate on the distal end axis Z1.
(Driving Mechanism for Jaws)

As illustrated in FIGS. 12 and 13, the interface 272 also has a first conversion mechanism 151, a second conversion mechanism 152, a first torque transmission unit 125, a first jaw driving pulley 126, a second jaw driving pulley 127, first guide pulleys 128a and 129a, and second guide pulleys 128b and 129b. In FIGS. 12 and 13, the second guide pulleys 128b and 129b are not illustrated because they are hidden by the base 116.

The second guide pulley 129b, as illustrated in FIG. 14, is disposed at a position opposite of the base 116 from the first guide pulley 129a. The second guide pulley 128b is disposed at a position opposite of the base 116 from the first guide pulley 128a.

Hereinafter, the first guide pulleys 128a and 129a and the second guide pulleys 128b and 129b are also simply called "guide pulleys".

Referring to FIGS. 12 and 13 again, the rotation axes of the first jaw driving pulley 126 and the second jaw driving pulley 127 are in parallel to each other and extend in directions orthogonal to the proximal end axis Z2. For example, the first jaw driving pulley 126 and the second jaw driving pulley 127 rotate on the same rotation axis. The first jaw driving pulley 126 and the second jaw driving pulley 127 have different rotation planes.

The first conversion mechanism 151 converts the torque of the rotation of the first jaw driving gear 112 into the torque to rotate the first jaw driving pulley 126. The second conversion mechanism 152 converts the torque of the rotation of the second jaw driving gear 113 into the torque to rotate the second jaw driving pulley 127.

More specifically, the first conversion mechanism 151 has the two bevel gears 121 and 122. The second conversion mechanism 152 has the two bevel gears 123 and 124.

The bevel gears 121, 122, 123, and 124 each has a conical surface, on which grooves are formed. The bevel gear 121 and the bevel gear 123 rotate on the proximal end axis Z2. The bevel gear 122 and the bevel gear 124 rotate on axes extending in directions orthogonal to the proximal end axis Z2.

The first torque transmission unit 125 passes through the inside of the wrist-portion driving gear 111 and is fixed to the bevel gear 121 and the first jaw driving gear 112. The bevel gear 121 is engaged with the bevel gear 122. The first jaw driving pulley 126 is fixed to the bevel gear 122.

When the first jaw driving gear 112 rotates according to an operation instruction from the controller 4 illustrated in FIG. 1, the first torque transmission unit 125 and the bevel gear 121 rotate on the proximal end axis Z2. Then, the rotation of the bevel gear 121 rotates the bevel gear 122 engaged with the bevel gear 121 and the first jaw driving pulley 126 fixed to the bevel gear 122, on an axis orthogonal to the proximal end axis Z2.

Then, the rotation of the first jaw driving pulley 126 drives the first jaw 22a illustrated in FIG. 7. The detailed structure to drive the first jaw 22a is described later.

In addition, as illustrated in FIG. 13, the interface 272 further has a second torque transmission unit 175. The second torque transmission unit 175 passes through the insides of the first torque transmission unit 125, wrist-portion driving gear 111, and first jaw driving gear 112 and is fixed to the bevel gear 123 and the second jaw driving gear 113. The bevel gear 123 is engaged with the bevel gear 124. The second jaw driving pulley 127 is fixed to the bevel gear 124.

When the second jaw driving gear 113 rotates according to an operation instruction from the controller 4 illustrated in FIG. 1, the second torque transmission unit 175 and the bevel gear 123 rotate on the proximal end axis Z2. Then, the rotation of the bevel gear 123 rotates the bevel gear 124 engaged with the bevel gear 123 and the second jaw driving pulley 127 fixed to the bevel gear 124, on an axis orthogonal to the proximal end axis Z2.

Then, the rotation of the second jaw driving pulley 127 drives the second jaw 22b illustrated in FIG. 7. The detailed structure to drive the second jaw 22b is described later.

As described above, the use of the first conversion mechanism 151 eliminates the need for coupling the first jaw driving gear 112 and the first jaw driving pulley 126, increasing the number of arrangement variations. Also as described above, the use of the second conversion mechanism 152 eliminates the need for coupling the second jaw driving gear 113 and the second jaw driving pulley 127, increasing the number of arrangement variations.

(a) Driving Mechanism for First Jaw

As illustrated in FIGS. 12 and 13, the driving device 271 in the surgical-tool driving mechanism 27 further has a first tension pulley 130a and a second tension pulley 130b. In FIGS. 12 and 13, the second tension pulley 130b is not illustrated because it is hidden by the base 116.

The second tension pulley 130b is disposed at a position opposite of the base 116 from the first tension pulley 130a. Hereinafter, the first tension pulley 130a and the second tension pulley 130b are also simply called the "tension pulleys".

The jaw operating wire 46 for driving the first jaw 22a is wound on the first jaw driving pulley 126. The first end 46a side of the jaw operating wire 46 is guided by the first guide pulley 128a and passes through the inside of the flexible shaft 2. Then, the first end 46a of the jaw operating wire 46 is fixed to the first jaw 22a illustrated in FIG. 11.

In addition, the second end 46b side of the jaw operating wire 46 is guided by the second guide pulley 128b and the second tension pulley 130b and passes through the inside of the flexible shaft 2. Then, the second end 46b of the jaw operating wire 46 is fixed to the first jaw 22a illustrated in FIG. 11.

Note that as illustrated in FIG. 13, between the first guide pulley 128a and the first jaw driving pulley 126 and between the first jaw driving pulley 126 and the second guide pulley 128b, the jaw operating wire 46 extends approximately in parallel with the proximal end axis Z2.

When the first jaw driving pulley 126 rotates, the jaw operating wire 46 moves, and the first jaw 22a pivots about the coupling axis 49.

The jaw operating wire 46 turns at its contact portions with the guide pulleys 128a and 128b. The angles of the bent portions (or turning portions) of the jaw operating wire 46 on the guide pulley 128a and 128b sides are larger than 90 degrees. If the angles are too large, it would make the surgical-tool driving mechanism 27 larger in the extending direction of the proximal end axis Z2. Thus, it is preferable that the angles be smaller than 120 degrees.

Since the guide pulleys 128a and 128b guide the jaw operating wire 46 with gentle angles, the jaw operating wire 46 can be driven more smoothly than, for example, in the case where the jaw operating wire 46 is guided to turn by 90 degrees. In addition, since the bent angles of the jaw operating wire 46 on the guide pulley 128a and 128b sides are smaller than or equal to 120 degrees, the wiring path of the jaw operating wire 46 is short, contributing to downsizing the surgical-tool driving mechanism 27.

(b) Driving Mechanism for Second Jaw

Referring to FIGS. 12 and 13 again, the surgical-tool driving mechanism 27 further has a first tension pulley 131a and a second tension pulley 131b. In FIGS. 12 and 13, the second tension pulley 131b is not illustrated because it is hidden by the base 116.

The second tension pulley 131b is disposed at a position opposite of the base 116 from the first tension pulley 131a. Hereinafter, the first tension pulley 131a and the second tension pulley 131b are also simply called the "tension pulleys".

The jaw operating wire 47 for driving the second jaw 22b is wound on the second jaw driving pulley 127. The first end 47a side of the jaw operating wire 47 is guided by the first guide pulley 129a and the first tension pulley 131a and passes through the inside of the flexible shaft 2. Then, the first end 47a of the jaw operating wire 47 is fixed to the second jaw 22b illustrated in FIG. 11.

In addition, the second end 47b side of the jaw operating wire 47 is guided by the second guide pulley 129b and the second tension pulley 131b and passes through the inside of the flexible shaft 2. Then, the second end 47b of the jaw operating wire 47 is fixed to the second jaw 22b illustrated in FIG. 11.

Note that as illustrated in FIG. 13, between the first guide pulley 129a and the second jaw driving pulley 127 and between the second jaw driving pulley 127 and the second guide pulley 129b, the jaw operating wire 47 extends approximately in parallel with the proximal end axis Z2.

When the second jaw driving pulley 127 rotates, the jaw operating wire 47 moves, and the second jaw 22b pivots about the coupling axis 49.

The jaw operating wire 47 turns at its contact portions with the guide pulleys 129a and 129b. The angles of the bent portions of the jaw operating wire 47 on the guide pulley 129a and 129b sides are larger than 90 degrees. If the angles are too large, it would make the surgical-tool driving mechanism 27 larger in the extending direction of the proximal end axis Z2. Thus, it is preferable that the angles be smaller than 120 degrees.

Since the guide pulleys 129a and 129b guide the jaw operating wire 47 with gentle angles, the jaw operating wire 47 can be driven more smoothly than, for example, in the case where the jaw operating wire 47 is guided to turn by 90 degrees. In addition, since the bent angles of the jaw operating wire 47 on the guide pulley 129a and 129b sides are smaller than or equal to 120 degrees, the wiring path of the jaw operating wire 47 is short, contributing to downsizing the surgical-tool driving mechanism 27.

Meanwhile, the bevel gears 121, 122, 123, and 124, the first jaw driving pulley 126, the second jaw driving pulley 127, the guide pulleys 128a, 128b, 129a, and 129b, the tension pulleys 130a, 130b, 131a, and 131b, the first conversion mechanism 151, and the second conversion mechanism 152 are attached to the base 116.

Thus, when the base 116 rotates on the proximal end axis Z2 along with the rotation of the wrist-portion driving gear 111 as described above, these members attached to the base 116 rotates together with the base 116 on the proximal end axis Z2.

In other words, when the wrist portion 23, first jaw 22a, and second jaw 22b illustrated in FIG. 11 rotate on the distal end axis Z1, the mechanism for driving the first jaw 22a and the mechanism for driving the second jaw 22b rotate on the proximal end axis Z2 in conjunction with the wrist portion 23, first jaw 22a, and second jaw 22b.

In addition, the first torque transmission unit 125 and the second torque transmission unit 175 illustrated in FIG. 13 rotate on the proximal end axis Z2, independently of the wrist-portion driving gear 111 for rotating the base 116. Thus, the first jaw 22a and the second jaw 22b can be driven independently of the rotation of the wrist portion 23.

(Driving Mechanism for Multi-Articulated Portion)

As illustrated in FIGS. 12 and 13, the surgical-tool driving mechanism 27 further has a first-multi-articulated-portion driving pulley 132, a second-multi-articulated-portion driving pulley 133, first guide pulleys 134a and 135a, second guide pulleys 134b and 135b, first tension pulleys 136a and 137a, and second tension pulleys 136b and 137b. In FIGS. 12 and 13, the second guide pulleys 134b and 135b are not illustrated because they are hidden by the frame 117.

As illustrated in FIG. 14, the second guide pulley 135b is disposed at a position opposite of the frame 117 from the first guide pulley 135a. The second guide pulley 134b is disposed at a position opposite of the frame 117 from the first guide pulley 134a.

Hereinafter, the first guide pulleys 134a and 135a and the second guide pulleys 134b and 135b are also simply called the "guide pulleys". In addition, the first tension pulleys 136a and 137a and the second tension pulleys 136b and 137b are also simply called the "tension pulleys".

In FIGS. 12 and 13, the second tension pulleys 136b and 137b are not illustrated because they are hidden by the frame 117. The second tension pulley 136b is disposed at a position opposite of the frame 117 from the first tension pulley 136a. The second tension pulley 137b is disposed at a position opposite of the frame 117 from the first tension pulley 137a.

The rotation axes of the first-multi-articulated-portion driving pulley 132 and the second-multi-articulated-portion driving pulley 133 are in parallel to each other and extend in directions orthogonal to the proximal end axis Z2. The first-multi-articulated-portion driving pulley 132 and the second-multi-articulated-portion driving pulley 133 have different rotation planes.

The first-multi-articulated-portion driving pulley 132 and the second-multi-articulated-portion driving pulley 133 are disposed outside the frame 117. This structure in which at least one of the driving pulleys in the surgical-tool driving mechanism 27 is disposed outside of the frame 117 as above is preferable because it is easy to wind an elongate element to the driving pulley.

(a) Driving Mechanism for First Multi-Articulated Portion

The first-multi-articulated-portion driving pulley 132 rotates in conjunction with the first-multi-articulated-portion driving gear 114. On the first-multi-articulated-portion driving pulley 132 is wound the multi-articulated portion operating wire 41a.

The first end side of the multi-articulated portion operating wire 41a is guided by the first guide pulley 134a and the first tension pulley 136a and passes through the inside of the flexible shaft 2. Then, the first end of the multi-articulated portion operating wire 41a is fixed to the distal end side fixing point 45a1 of the first multi-articulated portion 24a illustrated in FIG. 10B.

The second end side of the multi-articulated portion operating wire 41a is guided by the second guide pulley 134b and the second tension pulley 136b and passes through the inside of the flexible shaft 2. Then, the second end of the multi-articulated portion operating wire 41a is fixed to the distal end side fixing point 45a2 of the first multi-articulated portion 24a illustrated in FIG. 10B. Note that as illustrated in FIG. 10B, the distal end side fixing point 45a1 and the distal end side fixing point 45a2 are disposed with some distance in between.

As illustrated in FIG. 13, between the first guide pulley 134a and the first-multi-articulated-portion driving pulley 132 and between the first-multi-articulated-portion driving pulley 132 and the second guide pulley 134b, the multi-articulated portion operating wire 41a extends approximately in parallel with the proximal end axis Z2.

When the first-multi-articulated-portion driving gear 114 rotates, the first-multi-articulated-portion driving pulley 132 rotates on the axis orthogonal to the proximal end axis Z2. The rotation of the first-multi-articulated-portion driving pulley 132 moves the multi-articulated portion operating wire 41a, bending the first multi-articulated portion 24a illustrated in FIG. 10A.

The multi-articulated portion operating wire 41a turns at its contact portions with the guide pulleys 134a and 134b. The angles of the bent portions of the multi-articulated portion operating wire 41a on the guide pulley 134a and 134b sides are larger than 90 degrees. If the angles are too large, it would make the surgical-tool driving mechanism 27 larger in the extending direction of the proximal end axis Z2. Thus, it is preferable that the angles be smaller than 120 degrees.

Since the guide pulleys 134a and 134b guide the multi-articulated portion operating wire 41a with gentle angles, the multi-articulated portion operating wire 41a can be driven more smoothly than, for example, in the case where the multi-articulated portion operating wire 41a is guided to turn by 90 degrees. In addition, since the bent angles of the multi-articulated portion operating wire 41a on the guide pulley 134a and 134b sides are smaller than or equal to 120 degrees, the wiring path of the multi-articulated portion operating wire 41a is short, contributing to downsizing the surgical-tool driving mechanism 27.

(b) Driving Mechanism for Second Multi-Articulated Portion

The second-multi-articulated-portion driving pulley 133 rotates in conjunction with the second-multi-articulated-portion driving gear 115. On the second-multi-articulated-portion driving pulley 133 is wound the multi-articulated portion operating wire 41b.

The first end side of the multi-articulated portion operating wire 41b is guided by the first guide pulley 135a and the first tension pulley 137a and passes through the inside of the flexible shaft 2. Then, the first end of the multi-articulated portion operating wire 41b is fixed to the distal end side fixing point 45b1 of the second multi-articulated portion 24b illustrated in FIG. 10C.

The second end side of the multi-articulated portion operating wire 41b is guided by the second guide pulley 135b and the second tension pulley 137b and passes through the inside of the flexible shaft 2. Then, the second end of the multi-articulated portion operating wire 41b is fixed to the distal end side fixing point 45*b*2 of the second multi-articulated portion 24*b* illustrated in FIG. 10C. Note that as illustrated in FIG. 10C, the distal end side fixing point 45*b*1 and the distal end side fixing point 45*b*2 are disposed with some distance in between.

As illustrated in FIG. 13, between the first guide pulley 135*a* and the second-multi-articulated-portion driving pulley 133 and between the second-multi-articulated-portion driving pulley 133 and the second guide pulley 135*b*, the multi-articulated portion operating wire 41*b* extends approximately in parallel with the proximal end axis Z2.

When the second-multi-articulated-portion driving gear 115 rotates, the second-multi-articulated-portion driving pulley 133 rotates on the axis orthogonal to the proximal end axis Z2. The rotation of the second-multi-articulated-portion driving pulley 133 moves the multi-articulated portion operating wire 41*b*, bending the second multi-articulated portion 24*b* illustrated in FIG. 10A.

The multi-articulated portion operating wire 41*b* turns at its contact portions with the guide pulleys 135*a* and 135*b*. The angles of the bent portions of the multi-articulated portion operating wire 41*b* on the guide pulley 135*a* and 135*b* sides are larger than 90 degrees. If the angles are too large, it would make the surgical-tool driving mechanism 27 larger in the extending direction of the proximal end axis Z2. Thus, it is preferable that the angles be smaller than 120 degrees.

Since the guide pulleys 135*a* and 135*b* guide the multi-articulated portion operating wire 41*b* with gentle angles, the multi-articulated portion operating wire 41*b* can be driven more smoothly than, for example, in the case where the multi-articulated portion operating wire 41*b* is guided to turn by 90 degrees. In addition, since the bent angles of the multi-articulated portion operating wire 41*b* on the guide pulley 135*a* and 135*b* sides are smaller than or equal to 120 degrees, the wiring path of the multi-articulated portion operating wire 41*b* is short, contributing to downsizing the surgical-tool driving mechanism 27.

[Tension Adjusting Mechanism]

The jaw operating wires 46 and 47 may get loose or slack, for example, for the reason that tension is exerted on them for a long time. In particular, when large tensions are exerted on the jaw operating wires 46 and 47, such as when the first jaw 22*a* and second jaw 22*b* pinch something hard, the jaw operating wires 46 and 47 may get loose or slack to a large extent.

The multi-articulated portion operating wires 41*a* and 41*b* may also get loose or slack in the same way as the jaw operating wires 46 and 47. In particular, when large tensions are exerted on the multi-articulated portion operating wires 41*a* and 41*b*, such as when the multi-articulated portion 24 is bent at a large angle with respect to the proximal end axis Z2, the multi-articulated portion operating wires 41*a* and 41*b* may get loose or slack to a large extent.

A problem is that in the case where the jaw operating wire 46 gets loose or slack, the jaw operating wire 46 may come off the guide pulley 128*a* or 128*b*, or it may take some time for the jaw operating wire 46 to transmit torque, making unable to operate the first jaw 22*a* as desired.

Also in the case where the jaw operating wire 47, multi-articulated portion operating wire 41*a*, or multi-articulated portion operating wire 41*b* gets loose or slack, the same kind of problem occurs.

To address this problem, in the surgical-tool driving mechanism 27 one or more embodiments, the guide pulleys 128*a*, 128*b*, 129*a*, 129*b*, 134*a*, 134*b*, 135*a*, and 135*b* and the tension pulleys 130*a*, 130*b*, 131*a*, 131*b*, 136*a*, 136*b*, 137*a*, and 137*b* are provided with tension adjusting mechanisms which adjust the wire tensions, as described below.

(Structure of Tension Adjusting Mechanism)

(a) Tension Adjustment Mechanism for Jaw Operating Wires

Referring to FIGS. 12 and 13, the tension pulleys 130*a* and 130*b* are disposed closer to the flexible shaft 2 than the guide pulleys 128*a* and 128*b*. Each of the tension pulleys 130*a* and 130*b* is movable in the circumferential direction of a circle centered on the corresponding guide pulley 128*a* or 128*b* and is urged.

As illustrated in FIG. 13, the tension pulleys 130*a* and 130*b* are disposed in the paths of the jaw operating wire 46 from the guide pulleys 128*a* and 128*b* to the proximal end portion 2*a*. The tension pulleys 130*a* and 130*b* bias straight line portions of the jaw operating wire 46 in directions oblique to the straight line portions.

This structure improves the smoothness and endurance of driving the jaw operating wire 46, compared to, for example, the case of urging the jaw operating wire 46 by bending it at 90 degrees. In addition, there is no need for allocating a large space for the tension pulleys 130*a* and 130*b*, thus contributing to downsizing the driving mechanism 27 of the surgical tool.

The tension pulleys 131*a* and 131*b* are disposed closer to the flexible shaft 2 than the guide pulleys 129*a* and 129*b*. Each of the tension pulleys 131*a* and 131*b* is movable in the circumferential direction of a circle centered on the corresponding guide pulley 129*a* or 129*b* and is urged.

As illustrated in FIG. 13, the tension pulleys 131*a* and 131*b* are disposed in the paths of the jaw operating wire 47 from the guide pulleys 129*a* and 129*b* to the proximal end portion 2*a*. The tension pulleys 131*a* and 131*b* bias or urge straight line portions of the jaw operating wire 47 in directions oblique to the straight line portions.

This structure improves the smoothness and endurance of driving the jaw operating wire 47, compared to, for example, the case of urging the jaw operating wire 47 by bending it at 90 degrees. In addition, there is no need for allocating large spaces for the tension pulleys 131*a* and 131*b*, thus contributing to downsizing the driving mechanism 27 of the surgical tool.

More specifically, the tension pulleys 130*a* and 130*b* receive urging forces from not-illustrated elastic members, such as springs, and bias the jaw operating wire 46 in the directions that are circumferential directions of circles centered on the guide pulleys 128*a* and 128*b* and directions away from the proximal end axis Z2.

The tension pulleys 131*a* and 131*b* receive urging forces from not-illustrated elastic members, such as springs, and bias the jaw operating wire 47 in the directions that are circumferential directions of circles centered on the guide pulleys 129*a* and 129*b* and directions away from the proximal end axis Z2.

With this structure, when the tension exerted on the jaw operating wire 46 is larger than the urging forces generated by the elastic members, the tension pulleys 130*a* and 130*b* move, against the urging forces from the elastic members, in the directions that are circumferential directions of circles centered on the guide pulleys 128*a* and 128*b* and directions toward the proximal end axis Z2. This prevents the tension exerted on the jaw operating wire 46 from becoming too large.

On the other hand, when the tension exerted on the jaw operating wire 46 is smaller than the urging forces generated by the elastic members, the tension pulleys 130*a* and 130*b* move in the directions that are circumferential directions of circles centered on the guide pulleys 128*a* and 128*b* and directions away from the proximal end axis Z2. This prevents the tension exerted on the jaw operating wire 46 from becoming too small.

The tension exerted on the jaw operating wire 46 is stable as described above, preventing the jaw operating wire 46 from getting loose or slack without disturbing the movement of the jaw operating wire 46.

Similarly for the jaw operating wire 47, the tension pulleys 131a and 131b move in circumferential directions of circles centered on the guide pulleys 129a and 129b according to the magnitude of the tension exerted on the jaw operating wire 47.

This makes the tension exerted on the jaw operating wire 47 stable, preventing the jaw operating wire 47 from getting loose or slack without disturbing the movement of the jaw operating wire 47.

Note that the tension pulleys 130a and 130b may be deposed closer to the first jaw driving pulley 126 than the guide pulleys 128a and 128b. However, the structure in which the tension pulleys 130a and 130b are disposed in the spaces between the guide pulleys 128a and 128b and the proximal end portion 2a is preferable because space can be used effectively.

In addition, the tension pulleys 131a and 131b are disposed closer to the second jaw driving pulley 127 than the guide pulleys 129a and 129b. However, for the same reason as described above, the structure in which the tension pulleys 131a and 131b are disposed between the guide pulley 129a and 129b and the proximal end portion 2a is preferable.

In addition, the tension pulleys 130a, 130b, 131a, and 131b may be movable in the circumferential directions of circles centered on parts different from the guide pulleys 128a, 128b, 129a, and 129b.

(b) Tension Adjusting Mechanism for Multi-Articulated Portion Operating Wires

The tension pulleys 136a and 136b are disposed closer to the flexible shaft 2 than the guide pulleys 134a and 134b. Each of the tension pulleys 136a and 136b is movable in the circumferential direction of a circle centered on the corresponding guide pulley 134a or 134b and is urged.

As illustrated in FIG. 13, the tension pulleys 136a and 136b are disposed in the paths of the multi-articulated portion operating wire 41a from the guide pulleys 134a and 134b to the proximal end portion 2a. The tension pulleys 136a and 136b bias straight line portions of the multi-articulated portion operating wire 41a in directions oblique to the straight line portions.

This structure improves the smoothness and endurance of driving the multi-articulated portion operating wire 41a, compared to, for example, the case of urging the multi-articulated portion operating wire 41a by bending it at 90 degrees. In addition, there is no need for allocating a large space for the tension pulleys 136a and 136b, thus contributing to downsizing the driving mechanism 27 of the surgical tool.

The tension pulleys 137a and 137b are disposed closer to the flexible shaft 2 than the guide pulleys 135a and 135b. Each of the tension pulleys 137a and 137b is movable in the circumferential direction of a circle centered on the corresponding guide pulley 135a or 135b and is urged.

As illustrated in FIG. 13, the tension pulleys 137a and 137b are disposed in the paths of the multi-articulated portion operating wire 41b from the guide pulleys 135a and 135b to the proximal end portion 2a. The tension pulleys 137a and 137b bias straight line portions of the multi-articulated portion operating wire 41b in directions oblique to the straight line portions.

This structure improves the smoothness and endurance of driving the multi-articulated portion operating wire 41b, compared to, for example, the case of urging the multi-articulated portion operating wire 41b by turning it at 90 degrees. In addition, there is no need for allocating large spaces for the tension pulleys 137a and 137b, thus contributing to downsizing the driving mechanism 27 of the surgical tool.

More specifically, the tension pulleys 136a and 136b receive urging forces from not-illustrated elastic members, such as springs, and are urged in the directions that are circumferential directions of circles centered on the guide pulleys 134a and 134b and directions away from the proximal end axis Z2.

The tension pulleys 137a and 137b receive urging forces from not-illustrated elastic members, such as springs, and are urged in the directions that are circumferential directions of circles centered on the guide pulleys 135a and 135b and directions away from the proximal end axis Z2.

With this structure, when the tension exerted on the multi-articulated portion operating wire 41a is larger than the urging forces generated by the elastic members, the tension pulleys 136a and 136b move in the directions that are circumferential directions of circles centered on the guide pulleys 134a and 134b and directions toward the proximal end axis Z2. This prevents the tension exerted on the multi-articulated portion operating wire 41a from becoming too large.

On the other hand, when the tension exerted on the multi-articulated portion operating wire 41a is smaller than the urging forces generated by the elastic members, the tension pulleys 136a and 136b move in the directions that are circumferential directions of circles centered on the guide pulleys 134a and 134b and directions away from the proximal end axis Z2. This prevents the tension exerted on the jaw operating wire 46 from becoming too small.

The tension exerted on the multi-articulated portion operating wire 41a is stable as described above, preventing the multi-articulated portion operating wire 41a from getting loose or slack without disturbing the movement of the multi-articulated portion operating wire 41a.

Similarly for the multi-articulated portion operating wire 41b, the tension pulleys 137a and 137b move in circumferential directions of circles centered on the guide pulleys 135a and 135b according to the magnitude of the tension exerted on the multi-articulated portion operating wire 41b.

This makes the tension exerted on the multi-articulated portion operating wire 41b stable, preventing the multi-articulated portion operating wire 41b from getting loose or slack without disturbing the multi-articulated portion operating wire 41b.

Note that the tension pulleys 136a and 136b may be deposed closer to the first-multi-articulated-portion driving pulley 132 than the guide pulleys 134a and 134b. However, the structure in which the tension pulleys 136a and 136b are disposed in the spaces between the guide pulleys 134a and 134b and the proximal end portion 2a is preferable because space can be used effectively.

In addition, the tension pulleys 137a and 137b are disposed closer to the second-multi-articulated-portion driving pulley 133 than the guide pulleys 135a and 135b. However, for the same reason as described above, the structure in which the tension pulleys 137a and 137b are disposed between the guide pulley 135a and 135b and the proximal end portion 2a is preferable.

In addition, the tension pulleys 136a, 136b, 137a, and 137b may be movable in the circumferential directions of circles centered on parts different from the guide pulleys 134a, 134b, 135a, and 135b.

As described above, one or more embodiments can achieve a tension adjusting mechanism that is small but capable of adjusting the tension of an elongate element for driving an end effector, and an interface and driving mechanism including the tension adjusting mechanisms.

In the above, description has been provided for features of the driving mechanisms and tension adjusting mechanisms applied to the medical treatment instrument 101 including the guide tube 11 and the bundling tube 12. However, it goes without saying that the driving mechanism and the tension adjusting mechanism can be applied not only to medical treatment instruments 101 including a guide tube 11 and a bundling tube 12 but also to wide varieties of mechanisms for driving medical treatment instruments.

It should be understood that the above one or more embodiments are examples in all respects and is not restrictive. The scope of the invention is defined not by the above description but by the claims, and it is intended that the invention includes all modifications within the scope of the claims and equivalents thereof.

The invention claimed is:

1. A surgical tool comprising:
an end effector;
an elongate element that drives the end effector;
a hollow shaft that includes a proximal end portion and a distal end portion which is coupled to the end effector;
a driving member which the elongate element led via the shaft is wound on;
a guide pulley that is disposed between the proximal end portion of the shaft and the driving member, wherein an outer circumference of the guide pulley contacts and guides the elongate element; and
a tension pulley that is disposed between the proximal end portion of the shaft and the guide pulley, wherein an outer circumference of the tension pulley contacts and biases the elongate element, and wherein the tension pulley is movable in a circumferential direction of a circle centered on the guide pulley; and
further comprising a second guide pulley and a second tension pulley, wherein
the end effector includes a first jaw and a second jaw,
the elongate element includes a first portion and a second portion between the first jaw and the driving member,
the first portion and the second portion led via the shaft are wound on the driving member in opposite directions,
the outer circumference of the guide pulley contacts and guides the first portion of the elongate element,
an outer circumference of the second guide pulley contacts and guides the second portion of the elongate element,
the outer circumference of the tension pulley contacts and biases the first portion of the elongate element,
an outer circumference of the second tension pulley contacts and biases the second portion of the elongate element, and
the second tension pulley is movable in a circumferential direction of a circle centered on the second guide pulley, and
the surgical tool further comprises:
a second driving member;
a second elongate element that includes a third portion and a fourth portion between the second jaw and the second driving member, wherein the third portion and the fourth portion led via the shaft are wound on the second driving member in opposite directions;
a third guide pulley that is disposed between the proximal end portion of the shaft and the second driving member, wherein an outer circumference of the third guide pulley contacts and guides the third portion of the second elongate element;
a third tension pulley that is disposed between the proximal end portion of the shaft and the third guide pulley, wherein an outer circumference of the third tension pulley contacts and biases the third portion of the second elongate element;
a fourth guide pulley that is disposed between the proximal end portion of the shaft and the second driving member, wherein an outer circumference of the fourth guide pulley contacts and guides the fourth portion of the second elongate element;
a fourth tension pulley that is disposed between the proximal end portion of the shaft and the fourth guide pulley, wherein an outer circumference of the fourth tension pulley contacts and biases the fourth portion of the second elongate element, and
the fourth tension pulley is movable in a circumferential direction of a circle centered on the fourth guide pulley.

2. The surgical tool according to claim 1, wherein
the elongate element includes a bent portion at a contact portion with the guide pulley, and
an inner angle of the bent portion of the elongate element is larger than 90 degrees.

3. The surgical tool according to claim 1, wherein
the end effector includes a multi-articulated portion that is bendable, and
the surgical tool comprises:
the second elongate element that bends the multi-articulated portion;
the second guide pulley disposed between the proximal end portion of the shaft and the second driving member; and
the second tension pulley disposed between the proximal end portion of the shaft and the second guide pulley.

4. The surgical tool according to claim 1, wherein
the guide pulley guides the elongate element led from the proximal end portion of the shaft in a direction in parallel with a longitudinal direction of the proximal end portion of the shaft toward the driving member.

5. The surgical tool according to claim 1, comprising
a base rotatable on an axis extending in a longitudinal direction of the proximal end portion of the shaft, wherein
the end effector includes the first and second jaws and a wrist portion that supports the first and second jaws,
the wrist portion rotates on an axis extending a longitudinal direction of the wrist portion, and
the tension pulley and the guide pulley that guides the elongate element used for operation of the first and second jaws are provided on the base so as to rotate in conjunction with rotation of the wrist portion.

6. The surgical tool according to claim 1, wherein
the shaft is flexible.

7. The surgical tool according to claim 1, wherein
a pair of the guide pulley and the tension pulley are disposed at positions opposite to a pair of the second guide pulley and the second tension pulley, with reference to a plane passing an axis of the proximal end portion of the shaft, and a pair of the third guide pulley and the third tension pulley are disposed at positions opposite to a pair of the fourth guide pulley and the fourth tension pulley, respectively, with reference to the plane.

8. A surgical tool comprising:
an end effector including a multi-articulated portion that is bendable;
a flexible shaft that is hollow and includes a proximal end portion and a distal end portion which is coupled to the multi-articulated portion;
an elongate element that bends the multi-articulated portion;
a driving member which the elongate element led via the shaft is wound on;
a guide pulley that is disposed between the proximal end portion of the shaft and the driving member, wherein an outer circumference of the guide pulley contacts and guides the elongate element; and
a tension pulley that is disposed between the proximal end portion of the shaft and the guide pulley, wherein an outer circumference of the tension pulley contacts and biases the elongate element, wherein
the tension pulley is movable in a circumferential direction of a circle centered on the guide pulley;
further comprising a second guide pulley and a second tension pulley,
wherein the elongate element includes a first portion and a second portion between a first part of the multi-articulated portion and the driving member,
the first portion and the second portion led via the shaft are wound on the driving member in opposite directions,
the outer circumference of the guide pulley contacts and guides the first portion of the elongate element,
an outer circumference of the second guide pulley contacts and guides the second portion of the elongate element,
the outer circumference of the tension pulley contacts and biases the first portion of the elongate element,
an outer circumference of the second tension pulley contacts and biases the second portion of the elongate element,
the second tension pulley is movable in a circumferential direction of a circle centered on the second guide pulley, and
the surgical tool further comprises:
a second driving member;
a second elongate element that includes a third portion and a fourth portion between a second part of the multi-articulated portion and the second driving member, wherein the third portion and the fourth portion led via the shaft are wound on the second driving member in opposite directions;
a third guide pulley that is disposed between the proximal end portion of the shaft and the second driving member, wherein an outer circumference of the third guide pulley contacts and guides the third portion of the second elongate element;
a third tension pulley that is disposed between the proximal end portion of the shaft and the third guide pulley, wherein an outer circumference of the third tension pulley contacts and biases the third portion of the second elongate element;

a fourth guide pulley that is disposed between the proximal end portion of the shaft and the second driving member, wherein an outer circumference of the fourth guide pulley contacts and guides the fourth portion of the second elongate element; and
a fourth tension pulley that is disposed between the proximal end portion of the shaft and the fourth guide pulley, wherein an outer circumference of the fourth tension pulley contacts and biases the fourth portion of the second elongate element, and
the fourth tension pulley is movable in a circumferential direction of a circle centered on the fourth guide pulley.

9. The surgical tool according to claim 8, wherein
the guide pulley guides the elongate element led from the proximal end portion of the shaft in a direction in parallel with a longitudinal direction of the proximal end portion of the shaft toward the driving member.

10. The surgical tool according to claim 8, further comprising:
the second elongate element bending a second part of the multi-articulated portion that is different from a first part that the elongate element bends;
the second guide pulley disposed between the proximal end portion of the shaft and the second driving member; and
the second tension pulley disposed between the proximal end portion of the shaft and the second guide pulley.

11. The surgical tool according to claim 8, wherein
a pair of the guide pulley and the tension pulley are disposed at positions opposite to a pair of the second guide pulley and the second tension pulley, with reference to a plane passing an axis of the proximal end portion of the shaft, and
a pair of the third guide pulley and the third tension pulley are disposed at positions opposite to a pair of the fourth guide pulley and the fourth tension pulley, respectively, with reference to the plane.

12. A surgical system comprising:
surgical tools each including an end effector and a flexible shaft;
driving devices to which the surgical tools are attached respectively;
an outer tube that holds the shafts of the surgical tools; and
a supporting device including holding portions that hold the respective driving devices and a grasping portion that grasps the outer tube, wherein
each of the surgical tools includes:
the end effector;
an elongate element that drives the end effector;
the shaft that is hollow and includes a proximal end portion and a distal end portion which is coupled to the end effector;
a driving member which the elongate element led via the shaft is wound on;
a guide pulley that is disposed between the proximal end portion of the shaft and the driving member, wherein an outer circumference of the guide pulley contacts and guides the elongate element; and
a tension pulley that is disposed between the proximal end portion of the shaft and the guide pulley, wherein an outer circumference of the tension pulley contacts and biases the elongate element, and wherein the tension pulley is movable in a circumferential direction of a circle centered on the guide pulley;
further comprising a second guide pulley and a second tension pulley, wherein the elongate element includes a first portion and a second portion between a first part of a multi-articulated portion comprised in the end effector and the driving member, the first portion and the second portion led via the shaft are wound on the driving member in opposite directions, the outer circumference of the guide pulley contacts and guides the first portion of the elongate element, an outer circumference of the second guide pulley contacts and guides the second portion of the elongate element, the outer circumference of the tension pulley contacts and biases the first portion of the elongate element, an outer circumference of the second tension pulley contacts and biases the second portion of the elongate element, the second tension pulley is movable in a circumferential direction of a circle centered on the second guide pulley, and each of the surgical tools further comprises:

a second driving member;

a second elongate element that includes a third portion and a fourth portion between a second part of the multi-articulated portion and the second driving member, wherein the third portion and the fourth portion led via the shaft are wound on the second driving member in opposite directions;

a third guide pulley that is disposed between the proximal end portion of the shaft and the second driving member, wherein an outer circumference of the third guide pulley contacts and guides the third portion of the second elongate element;

a third tension pulley that is disposed between the proximal end portion of the shaft and the third guide pulley, wherein an outer circumference of the third tension pulley contacts and biases the third portion of the second elongate element;

a fourth guide pulley that is disposed between the proximal end portion of the shaft and the second driving member, wherein an outer circumference of the fourth guide pulley contacts and guides the fourth portion of the second elongate element; and a fourth tension pulley that is disposed between the proximal end portion of the shaft and the fourth guide pulley, wherein an outer circumference of the fourth tension pulley contacts and biases the fourth portion of the second elongate element, and the fourth tension pulley is movable in a circumferential direction of a circle centered on the fourth guide pulley.

13. The surgical system according to claim 12, wherein each of the driving devices includes a driving source and a transmission member that transmits force generated by driving the driving source, and each of the surgical tools includes a transmission-counterpart member that is engaged with the transmission member and receives force transmitted from the transmission member to rotate the driving member.

14. The surgical system according to claim 12, wherein the outer tube includes guide tubes into which the respective surgical tools are inserted, each of the guide tubes is flexible and includes a protruding portion that protrudes from a distal end of the outer tube, and the end effector of each of the surgical tools is insertable into a body of a patient via the corresponding guide tube.

\* \* \* \* \*

UNITED STATES PATENT AND TRADEMARK OFFICE
CERTIFICATE OF CORRECTION

| | | |
|---|---|---|
| PATENT NO. | : 11,219,496 B2 | Page 1 of 1 |
| APPLICATION NO. | : 16/262949 | |
| DATED | : January 11, 2022 | |
| INVENTOR(S) | : Ito et al. | |

It is certified that error appears in the above-identified patent and that said Letters Patent is hereby corrected as shown below:

On the Title Page

Insert item (30):
--(30) Foreign Application Priority Data
Mar. 24, 2017 (JP) .......................... JP2017-059891--

Signed and Sealed this
Fifth Day of July, 2022

Katherine Kelly Vidal
*Director of the United States Patent and Trademark Office*